United States Patent [19]

Lacroix et al.

[11] 4,115,559

[45] Sep. 19, 1978

[54] DIPHOSPHORUS DERIVATIVES AND FUNGICIDAL COMPOSITIONS CONTAINING THEM

[75] Inventors: Guy Lacroix, Lyon; Jean-Claude Debourge, Courbevoie; Jacques Ducret, Lyon, all of France

[73] Assignee: Philagro S.A., France

[21] Appl. No.: 654,052

[22] Filed: Jan. 30, 1976

[30] Foreign Application Priority Data

Feb. 5, 1975 [FR] France .................... 75 04394

[51] Int. Cl.$^2$ .................... A01N 9/36
[52] U.S. Cl. .................... 424/209; 424/DIG. 8
[58] Field of Search .................... 424/209, DIG. 8

[56] References Cited

U.S. PATENT DOCUMENTS 3,740,427  6/1973  Hoffmann et al. .................... 424/209

FOREIGN PATENT DOCUMENTS 1,036,251  8/1958  Fed. Rep. of Germany.

OTHER PUBLICATIONS

Edmundson, Chem. Abst., vol. 63, (1965) 7013-7014.
Zwierzah, Canadian J. of Chem., vol. 45, (1967), pp. 2501-2512.
Krawiecki et al., J. Chem. Soc., 1960, pp. 881-885.
Houbew-Weyl, vol. XII/2, pp. 84-87, (1964).
Edmundson et al., J. Chem. Soc. 1966, pp. 1997-2003.

*Primary Examiner*—Allen J. Robinson

*Attorney, Agent, or Firm*—Robert E. Burns; Emmanuel J. Lobato; Bruce L. Adams

[57] ABSTRACT

Compositions and methods for their use are described for controlling parasitic fungi in and on plants containing, as active material, at least one compound corresponding to the formula

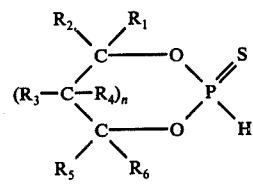

in which $R_1$, $R_2$, $R_3$, $R_4$, $R_5$ and $R_6$, which may be the same or different, represent hydrogen; halogen; nitro; alkyl, halo-alkyl or alkoxy carbonyl radical containing from 1 to 5 carbon atoms, and $n = 0$ or $1$.

The compositions are topically and systemically active and are applied to the susceptible plants, seeds, soil or its transportation or handling means and may be associated with an agricultural vehicle which facilitates its application. Compositions may also contain other agriculturally acceptable components including insecticides and other fungicides.

11 Claims, No Drawings

DIPHOSPHORUS DERIVATIVES AND FUNGICIDAL COMPOSITIONS CONTAINING THEM

This invention relates to fungicide compositions based on cyclic thiophosphites.

More particularly, the invention relates to compositions suitable for use in controlling parasitic fungi in plants and containing, as active material, at least one compound corresponding to the formula

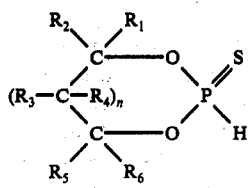

in which
$R_1$, $R_2$, $R_3$, $R_4$, $R_5$ and $R_6$, which may be the same or different, represent a hydrogen atom or halogen atom, a nitro group, an alkyl, halogen alkyl or alkoxy carbonyl radical containing from 1 to 5 carbon atoms and preferably from 1 to 3 carbon atoms, and
$n = 0$ or $1$.

When $n = 0$, the compounds may be called 2-thio-2H-1,3,2-dioxaphospholanes. When $n = 1$, they are called 2-thio-2H-1,3,2-dioxaphosphorinanes. In addition, $R_1$ and $R_5$ when $n = 0$, or $R_1$ and $R_3$ when $n = 1$, may together form a phenyl or naphthyl group.

These compounds are known per se as intermediates for the production of other phosphorus-containing compounds. The literature describes several methods of synthesis, cf. in particular Houben-Weyl, Vol. XII/2, pp. 84 to 87.

It is possible to treat a cyclic phosphite with phosphorus pentasulphide. This method is described by Yamasaki in Sci. Rep. Tohoku Univ., p. 73 (1959).

One method of synthesis commonly used comprises reacting hydrogen sulphide with a cyclic phosphite. The reaction is carried out in an organic solvent in the presence of a tertiary base, such as pyridine or triethylamine, at a temperature in the range from $-20°$ to $+100°$ C.

This reaction is described by J. Michalski and C. Krawiecki in J. Chem. Soc. 1960, p. 881, and also in DAS 1,036,251 (1965), and may take place in accordance with the following scheme:

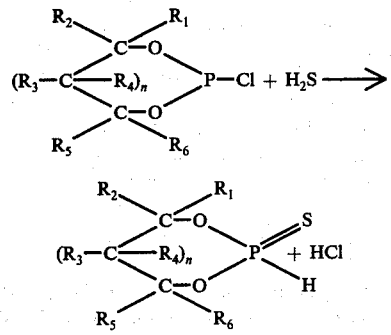

The following compounds were obtained by this method:

2-Thio-2H-4-methyl-1,3,2-dioxaphospholane (compound 1)

0.5 M (39.5 g) of pyridine in solution in 50 ml of anhydrous toluene is added with stirring to a solution of 0.5 M (70.2 g) of 2-chloro-4-methyl-1,3,2-dioxaphospholane in 200 ml of anhydrous toluene cooled to a temperature of $-10°$ C. After this addition, a stream of $H_2S$ is passed through the toluene solution for 2 hours during which the temperature is kept at $-10°$ C. Pyridinium hydrochloride is precipitated. After the stream of $H_2S$ has been cut off, nitrogen is passed through the reaction mixture for 2 hours during which the reactants are allowed to return to ambient temperature. The precipitate is filtered and the solvent is removed from the filtrate under reduced pressure, leaving a clear yellow oil which is distilled under reduced pressure:

Yield: 67%
Boiling point: 67°–68° C/0.2 mm Hg
$n_D^{20}$: 1.515

| Analysis | Centesimal analysis for $C_3H_7O_2PS$ | | | |
|---|---|---|---|---|
| | C % | H % | P % | S % |
| Calculated: | 26.1 | 5.07 | 22.45 | 23.20 |
| Observed: | 26.26 | 5.14 | 22.46 | 23.10 |

The following compounds were similarly prepared:

2-Thio-2H-1,3,2-dioxaphospholane (compound 2)

Yield: 30%
$n_D^{20}$: 1.530

| Analysis | Centesimal analysis for $C_2H_5O_2PS$ | | | |
|---|---|---|---|---|
| | C % | H % | P % | S % |
| Calculated: | 19.35 | 4.03 | 25.0 | 25.8 |
| Observed: | 19.41 | 4.06 | 25.08 | 25.73 |

2-Thio-2H-4,5-dimethyl-1,3,2-dioxaphospholane (compound 3)

Yield: 83%
$n_D^{20}$: 1.197

| Analysis | Centesimal analysis $C_4H_9O_2PS$ | | | |
|---|---|---|---|---|
| | C % | H % | P % | S % |
| Calculated: | 31.58 | 5.92 | 20.39 | 21.05 |
| Observed: | 31.80 | 5.94 | 20.31 | 20.99 |

2-Thio-2H-1,3,2-dioxaphosphorinane (compound 4)

Yield: 68%
Melting point: 33° C

| Analysis | Centesimal analysis for $C_3H_7O_2PS$ | | | |
|---|---|---|---|---|
| | C % | H % | P % | S % |
| Calculated: | 26.09 | 5.07 | 22.46 | 23.11 |
| Observed: | 26.05 | 5.08 | 22.45 | 23.20 |

2-Thio-2H-5,5-dimethyl-1,3,2-dioxaphosphorinane (compound 5)

Yield: 56%
Melting point: 84° C

| Centesimal analysis for $C_5H_{11}O_2PS$ | | | | |
| --- | --- | --- | --- | --- |
| Analysis | C % | H % | P % | S % |
| Calculated: | 36.14 | 6.63 | 18.67 | 19.28 |
| Observed: | 36.54 | 6.24 | 18.78 | 19.40 |

2-Thio-2H-4-methyl-1,3,2-dioxaphosphorinane (compound 6)

Yield: 51%
Boiling point: 72°-73° C/0.1 mm Hg
$n_D^{20}$: 1.5425

| Centesimal analysis for $C_4H_9O_2PS$ | | | | |
| --- | --- | --- | --- | --- |
| Analysis | C % | H % | P % | S % |
| Calculated: | 31.6 | 5.9 | 20.4 | 21.0 |
| Observed: | 31.7 | 6.0 | 20.8 | 21.1 |

2-Thio-2H-4,6-dimethyl-1,3,2-dioxaphosphorinane (compound 7)

Yield: 60%
Boiling point: 89°-94° C/0.04 mm Hg
$n_D^{20}$: 1.512

| Centesimal analysis for $C_5H_{11}O_2PS$ | | | | |
| --- | --- | --- | --- | --- |
| Analysis | C % | H % | P % | S % |
| Calculated: | 36.12 | 6.62 | 18.66 | 19.26 |
| Observed: | 36.10 | 6.80 | 18.63 | 19.36 |

2-Thio-2H-4-n-propyl-5-ethyl-1,3,2-dioxaphosphorinane (compound 8)

Yield: 75%
Boiling point: 112° C/0.025 mm Hg
$n_D^{20}$: 1.5045

| Centesimal analysis for $C_8H_{16}O_2PS$ | | | | |
| --- | --- | --- | --- | --- |
| Analysis | C % | H % | P % | S % |
| Calculated: | 46.10 | 8.17 | 14.90 | 15.40 |
| Observed: | 46.10 | 7.99 | 14.10 | 14.34 |

2-Thio-2H-4,5-benzo-1,3,2-dioxaphosphorinane (compound 9)

Yield: 100%
Melting point: 56° C

| Centesimal analysis for $C_7H_7O_2PS$ | | | | |
| --- | --- | --- | --- | --- |
| Analysis | C % | H % | P % | S % |
| Calculated: | 45.20 | 3.76 | 16.66 | 17.20 |
| Observed: | 45.09 | 3.86 | 16.74 | 17.31 |

It has now been found that the compounds have remarkable fungicidal properties, as shown by the following Examples.

EXAMPLE 1: In vivo test on *Plasmopara viticola* in vine plants (a) Preventive treatment Using a spray gun, the leaves of pot-grown vine plants (Gamay variety) are sprayed underneath with an aqueous suspension of a wettable powder having the following composition (by weight):

| | |
| --- | --- |
| active material to be tested | 20 % |
| deflocculant (calcium lignosulphate) | 5 % |
| wetting agent (sodium alkylaryl sulphonate) | 1 % |
| filler (aluminium silicate) | 74 % |

This suspension is diluted to the required extent and contains the active material to be tested in the dose in question. Each test was repeated three times.

After 48 hours, the plants are contaminated by spraying the leaves underneath with an aqueous suspension containing approximately 80,000 units/cc of spores of the fungus.

The pots are then stored for 48 hours in an incubation cell at 20° C/100% relative humidity.

The plants are inspected 9 days after infestation.

Under these conditions, it is found that, in a dose of 0.5 g/l, compounds 1 to 9 afford complete protection. In addition, it is pointed out that none of the compounds showed the least sign of phytotoxicity.

(b) Systemic test by root absorption on vine mildew

Several vine stocks (Gamay variety), each accommodated in a container filled with vermiculite and a nutritive solution, are sprayed with 40 cc of a 0.5 g/l solution of the material to be tested. After 2 days, the vine stocks are contaminated with an aqueous suspension containing 100,000 spores/cc of *Plasmopara viticola*. This is followed by incubation for 48 hours in a room at 20° C/100% relative humidity. The degree of infestation is inspected after about 9 days relative to an infested control which had been sprayed with 40 cc of distilled water.

Under these conditions, it is found that, in the dose of 0.5 g/l, compounds 1 to 6, which are absorbed by the roots, provide the vine leaves with complete protection against mildew, which clearly demonstrates the systemic nature of these compounds.

EXAMPLE 2: In vivo test on *Uromyces appendiculatus*

10 to 12 day old bean plants (Contender variety), grown in twos in 7 cm diameter pots, are used for the test.

Using a spray gun, the fungicidal treatment is carried out by spraying the leaves underneath with a suspension containing 0.5 g/l and 0.25 g/l of active material. The treatment is repeated twice per product and plants are kept as controls.

The plants are contaminated 48 hours afterwards by spraying the leaves underneath with a suspension containing approximately 80,000 spores/cc. The pots are then placed in a humid incubation cell for a period of 48 hours.

The plants are inspected about 10 to 15 days after infection.

For the systemic test, the compound is applied in the starting dose of 1 g/l of active material to the top of the leaf 48 hours before contamination.

Under these conditions, compounds 1 to 6 show excellent preventive activity coupled with good systemic activity.

EXAMPLE 3: In vivo test on *Erisyphe cichoracearum*

8 to 10 day old gherkin plants (variety: Petit Vert de Paris), grown in groups of 5 - 6 in 7 cm diameter pots, are used for the test.

Using a spray gun, the fungicidal treatment is carried out by spraying the plant as a whole with a suspension of 1 g/l/m.a.i. The treatment is repeated twice per product.

The plants are contaminated 48 hours afterwards by dusting starting with previous control plants. The pots are then placed on a bench for inspection.

The plants are inspected about 10 to 15 days after infection.

Under these conditions, compounds 1 to 6 show excellent fungicidal activity.

EXAMPLE 4: In vitro test on spore germination

The compounds according to the invention are studied for their effect on the germination of spores of the following fungi:

*Fusarium oxysporum*, responsible for tracheomycosis,
*Botrytis cinerea*, responsible for grey rot,
*Colletotrichum lagenarium*, responsible for anthracnosis in curcubitacea,
*Piricularia oryzae*, responsible for piriculariosis in rice,
*Uromyces appendiculatus*, responsible for bean rot.

The following procedure is adopted for each test: an acetone solution containing 0.1 g/l of the material to be tested is sprayed onto plates of glass. Following evaporation of the acetone, an aqueous suspension containing approximately 80,000 spores/cc of the fungus is applied to the plates of glass.

If the material to be tested is insoluble in acetone, a mixture of one volume of the above aqueous suspension and one volume of an aqueous suspension, containing 0.1 g/l of the material to be tested, of a wettable powder with the following composition, is applied to the plates of glass:

| active material to be tested | 20 % |
| defloceulant (calcium lignosulphate) | 5 % |
| wetting agent (sodium alkylaryl sulphonate) | 1 % |
| filler (aluminium silicate) | 74 % |

This wettable powder is then mixed with a quantity of water calculated for one application in the required dose.

The spores are then left to incubate for 24 hours at 20° C in an atmosphere of 100% relative humidity.

The number of spores which have germinated is then assessed, the result being expressed as percentage germination relative to an untreated control.

Under these conditions, it is found that, in a dose of 0.05 g/l, compounds 1 to 8 completely inhibit the germination of all the fungi used for this test.

EXAMPLE 5: In vitro test on mycelian growth

The following procedure is adopted for each test:

A suspension in gelose (agar-agar) containing approximately 70,000 spores/cc of the fungus is poured into a Petri dish at a temperature of about 50° C. This suspension is left to harden, after which discs of filter paper, impregnated with a suspension of the active material to be tested in various concentrations, are placed on it. The active material is in the form of a wettable powder prepared in accordance with Example 4.

A Petri dish containing discs saturated with distilled water is used as control.

Under these conditions, the following results are obtained:

in a dose of 0.25 g/l, compounds 1 to 6 totally inhibit the following fungi:

*Pythium de Baryanum*, responsible for the damping off of seedlings,

*Rhizoctonia solani*, responsible for necrosis of the neck;

in a dose of 0.01 g/l, the compounds still effectively inhibit the growth of *Pythium de Baryanum;* in a dose of 0.1 g/l, compound no. 1 is also totally effective against:

*Fusarium oxysporum*, responsible for tracheomycosis,
*Sclerotinia sclerotiorum*, responsible for sclerotiniosis,
*Verticillium dalhiae*, responsible for verticilliosis,
*Cercosporella herpotrichoides*, responsible for eyespot,
*Helminthosporium*, responsible for helminthosporiosis,
*Botrytis cinerea*, responsible for grey rot of the vine,
*Collectotrichum lagenarium*, responsible for anthracnosis of the melon.

These Examples demonstrate the remarkable fungicidal properties of the compounds according to the invention which are characterised by an immediate and systemic action on mildew of the vine, coupled with the complete absence of phytotoxicity. Interesting results have also been obtained in tests carried out on tobacco mildew and hop mildew. The compounds according to the invention have also proved to be extremely effective against other types of parasitic fungi, such as: *Peronospora tabacci, Pseudoperonospora humili, Phytophthora cactorum, Phytophthora capsici, Bremia lactucae, Phytophthora infestans,* Peronospora sp., *Phytophthora palmivora, Phytophthora phaseoli, Phytophthora megasperma, Phytophthora drechsteri* and other Phytophthora sp. in plants grown in temperate or tropical climates, such as tobacco, hops, on market-gardening plants, especially starwberries, pimentos, onions, peppers, tomatoes, beans, on ornamental plants, on pineapples, soya, citrus, cacao trees, coconut palms, hevea.

Accordingly, these compounds are particularly suitable for use in the preventive or curative treatment of fungus disease in plants, especially mildews, rusts and blights.

The compounds according to the invention may be used with advantage in admixture with one another or with other known fungicides, such as the metallic dithiocarbamates (manebe, zinebe, mancozebe), the basic salts or hydroxides of copper (oxychloride, oxysulphate), the (tetrahydro)-phthalimides (captane, captafol, folpel), methyl-N-(1-butylcarbamoyl)-2-benzimidazole carbamate (benomyl), 1,2-di-(3-methoxy or ethoxy)-carbonyl-2-thioureidobenzenes (thiophanates), methyl 2-benzimidazole carbamate, etc., either for completing the range of activity of the compounds according to the invention or for increasing their persistence.

The doses in which the compounds according to the invention are used may vary within wide limits according to the virulence of the fungus and the climatic conditions. Generally, doses of from 0.01 to 5 g/l of active material are suitable.

For their practical application, the compounds according to the invention are rarely used on their own. In most cases, they form part of formulations which generally contain a support and/or a surfactant in addition to the active material according to the invention.

In the context of the invention, a "support" is an organic or mineral, natural or synthetic material with which the active material is associated to facilitate its application to the plant, to seeds or to the soil, or its transportation or handling. The support may be solid (clays, natural or synthetic silicates, resins, waxes, solid fertilisers . . . . .) or fluid (water, alcohols, ketones, petroleum fractions, chlorinated hydrocarbons, liquefied gases).

The surfactant may be an ionic or non-ionic emulsifier, dispersant or wetting agent. Examples of suitable surfactants are salts of polyacrylic acids, lignin sulphonic acids, condensates of ethylene oxide or with fatty alcohols, fatty acids or fatty amines.

The compositions according to the invention may be prepared in the form of wettable powders, powders for dusting, granules, solutions, emulsifiable concentrates, emulsions, suspended concentrates and aerosols.

The wettable powders are normally prepared in such a way that they contain from 20 to 95% by weight of active material, and normally contain, in addition to a solid support, from 0 to 5% by weight of a wetting agent, from 3 to 10% by weight of a dispersant and, when necessary, from 0 to 10% by weight of one or more stabilisers and/or other additives, such as penetration agents, adhesives or antilumping agents, colorants, etc. The composition of a wettable powder is shown by way of example below:

| | |
|---|---|
| active material | 50 % |
| calcium lignosulphate (deflocculant) | 5 % |
| anionic wetting agent | 1 % |
| antilumping silica | 5 % |
| kaolin (filler) | 39 % |

Aqueous dispersions and emulsions, for example compositions obtained by diluting with water a wettable powder or an emulsifiable concentrate according to the invention, are included within the general scope of the present invention. These emulsions may be of the water-in-oil type or of the oil-in-water type and may have a thick consistency resembling that of a "mayonnaise".

The compositions according to the invention may contain other ingredients, for example protective colloids, adhesives or thickeners, thixotropic agents, stabilisers or sequestrants, and also other active materials known to have pesticidal properties, in particular acaricides or insecticides.

We claim:

1. A method for controlling the growth of fungus in plants which comprises contacting said plants with a fungicidally effective amount of at least one compound of the formula:

$$\begin{array}{c} R_2 \quad R_1 \\ \diagdown \diagup \\ C \text{---} O \\ \diagup \quad \diagdown \quad \diagup S \\ (R_3\text{---}C\text{---}R_4)_n \quad P \\ \diagdown \quad \diagup \quad \diagdown \\ C \text{---} O \quad H \\ \diagup \quad \diagdown \\ R_5 \quad R_6 \end{array}$$

wherein $R_1$, $R_2$, $R_3$, $R_4$, $R_5$ and $R_6$, which may be the same or different, represent hydrogen, or alkyl of from 1 to 5 carbon atoms, and $n = 0$ or 1;

and wherein $R_1$ and $R_5$ when $n = 0$, or $R_1$ and $R_3$ when $n = 1$, may together form a phenyl group.

2. The method of claim 1, wherein $R_1$ to $R_6$, which may be the same or different, represent hydrogen or alkyl of 1 to 3 carbon atoms.

3. The method of claim 2, wherein at least one of each of the groups $R_1$, $R_2$ and $R_5$, $R_6$ is hydrogen.

4. The method of claim 2, wherein $n = 0$ and said compound is a 2-thio-2H-1,3,2-dioxaphospholane wherein at least one each of said groups $R_1$, $R_2$ and $R_5$, $R_6$ is hydrogen.

5. The method of claim 4, wherein said compound is 2-thio-2H-4,5-dimethyl-1,3,2-dioxaphospholane.

6. The method of claim 4 wherein said compound is 2-thio-2H-1,3,2-dioxaphospholane.

7. The method of claim 4 wherein said compound is 2-thio-2H-4-methyl-1,3,2-dioxaphospholane.

8. The method of claim 2, wherein $n = 1$ and said compound is a 2-thio-2H-1,3,2-dioxaphosphorinane wherein at least one each of said groups $R_1$, $R_2$ and $R_5$, $R_6$ is hydrogen.

9. The method of claim 8 wherein said compound is 2-thio-2H-4,6dimethyl-1,3,2-dioxaphosphorinane.

10. The method of claim 8, wherein said compound is 2-thio-2H-1,3,2-dioxaphosphorinane.

11. The method of claim 8 wherein said compound is 2-thio-2H-4methyl-1,3,2-dioxaphosphorinane.

* * * * *